(12) United States Patent
Watanabe (10) Patent No.: US 8,184,162 B2
(45) Date of Patent: May 22, 2012

(54) RADIATION IMAGE CAPTURING APPARATUS

(75) Inventor: Koji Watanabe, Hadano (JP)

(73) Assignee: FUJIFILM Corporation, Tokyo (JP)

( * ) Notice: Subject to any disclaimer, the term of this patent is extended or adjusted under 35 U.S.C. 154(b) by 736 days.

(21) Appl. No.: 12/239,330

(22) Filed: Sep. 26, 2008

(65) Prior Publication Data

US 2009/0086026 A1 Apr. 2, 2009

(30) Foreign Application Priority Data

Sep. 27, 2007 (JP) ................................. 2007-252101

(51) Int. Cl.
*H04N 5/30* (2006.01)
(52) U.S. Cl. ................................... 348/162; 250/370.09
(58) Field of Classification Search .................. 348/162; 250/370.09
See application file for complete search history.

(56) References Cited

U.S. PATENT DOCUMENTS

| | | | |
|---|---|---|---|
| 4,857,723 A | 8/1989 | Modisette | |
| 6,265,720 B1 * | 7/2001 | Yamazaki et al. | 250/370.09 |
| 6,476,394 B1 * | 11/2002 | Amitani et al. | 250/370.11 |
| 7,317,189 B2 | 1/2008 | Miyazaki et al. | |
| 7,466,345 B2 * | 12/2008 | Kameshima et al. | 348/162 |
| 2003/0043064 A1 * | 3/2003 | Kuwabara | 341/155 |
| 2005/0220268 A1 * | 10/2005 | Fujii et al. | 378/114 |
| 2005/0273366 A1 * | 12/2005 | Ohara | 705/3 |
| 2006/0017826 A1 | 1/2006 | Sekimoto et al. | |
| 2008/0122925 A1 | 5/2008 | Sekimoto et al. | |

FOREIGN PATENT DOCUMENTS

| | | |
|---|---|---|
| JP | 61-198981 A | 9/1986 |
| JP | 10-206553 A | 8/1998 |
| JP | 2000-287034 A | 10/2000 |
| JP | 2001-045382 A | 2/2001 |
| JP | 2002-185720 A | 6/2002 |
| JP | 2005-349187 A | 12/2005 |
| JP | 2006-026234 A | 2/2006 |
| JP | 2007-166319 A | 6/2007 |

OTHER PUBLICATIONS

Rejection of the Application, dated Nov. 15, 2011, issued in corresponding JP Application No. 2007-252101, 3 pages in English and Japanese.

* cited by examiner

*Primary Examiner* — Philip B Tran
(74) *Attorney, Agent, or Firm* — Sughrue Mion, PLLC (57) ABSTRACT

A radiation image capturing apparatus includes: a radiation detector for detecting charge information; an analog multiplexer for passing an analog charge information signal read out from each pixel of the radiation detector, alternately in a first order and a second order opposite to the first order; an analog signal amplifier for amplifying the analog charge information signal; an analog/digital converter for converting the analog charge information signal to a corresponding digital charge information signal; and a signal correcting unit for using one of a first digital charge information signal corresponding to the analog charge information signal that has passed through the analog multiplexer in the first order and a second digital charge information signal corresponding to the analog charge information signal that has passed through the analog multiplexer in the second order, to correct the other of the first digital charge information signal and the second digital charge information signal.

7 Claims, 8 Drawing Sheets

RADIATION IMAGE CAPTURING APPARATUS

BACKGROUND OF THE INVENTION

1. Field of the Invention

The present invention relates to a radiation image capturing apparatus including a radiation detector for detecting charge information representing radiation image information. More specifically the present invention relates to a radiation image capturing apparatus which processes a signal from the radiation detector to prevent deterioration in the image quality of the radiation image.

2. Description of the Related Art

In the medical field, radiation image capturing apparatus is extensively used which exposes a subject (patient) to radiation and detects the radiation that has passed through the subject with a radiation detector in order to acquire a radiation image.

One example of such a radiation image capturing apparatus includes a radiation detector having linear electrodes formed therein. Charge information representing an electrostatic latent image stored in the radiation detector is read out by applying reading light that is perpendicular to the longitudinal direction of the linear electrodes over the length of the electrodes (see, for instance, the description of U.S. Pat. No. 4,857,723 and Japanese Laid-Open Patent Publication No. 2000-287034).

The description of U.S. Pat. No. 4,857,723 is directed to a radiation detector used in image capturing apparatus of the type described above. The radiation detector detects a current generated by each pixel when LED light is applied to the linear electrodes simultaneously as charge information representing the electrostatic latent image, and outputs the charge information via an analog multiplexer and an analog/digital converter (hereinafter referred to as an "A/D" converter).

Japanese Laid-Open Patent Publication No. 2000-287034 discloses a method and an apparatus for solving problems relating to the configuration recorded in U.S. Pat. No. 4,857,723. Specifically, the analog multiplexer recorded in the description of U.S. Pat. No. 4,857,723 causes deterioration in image quality due to noise generated when switching between pixel signals. To solve this problem, Japanese Laid-Open Patent Publication No. 2000-287034 proposes the provision of a different A/D converter for each linear electrode.

From Japanese Laid-Open Patent Publication No. 2000-287034, it is clear that the invention recorded in the description of U.S. Pat. No. 4,857,723 has a problem caused by noise when switching between signals in the analog multiplexer. In addition, there are concerns about how the responsiveness of an analog amplifier provided downstream of the analog multiplexer affects the image information. In particular, when an increase in overall throughput speed necessitates an increase in the switching speed of the analog multiplexer, problems such as blurring and loss of sharpness in image caused by poor responsiveness of the analog amplifier, occur at image edges and other portions with high contrast.

According to the invention recorded in Japanese Laid-Open Patent Publication No. 2000-287034, however, an analog multiplexer is not required and so the problems caused by noise when switching between signals in an analog multiplexer are eliminated. However, the invention of Japanese Laid-Open Patent Publication No. 2000-287034 has a disadvantage in that when an A/D converter is provided for each linear electrode rather than being provided singly in the manner of U.S. Pat. No. 4,857,723, the increase in scale of the printed circuit board leads to increases in occupied space and cost.

SUMMARY OF THE INVENTION

It is an object of the present invention to provide a radiation image capturing apparatus for which deterioration in image quality caused by switching between signals in an analog multiplexer and poor responsiveness of an analog signal amplifier can be avoided.

The radiation image capturing apparatus of the invention includes: a radiation detector for detecting charge information representing radiation image information; an analog multiplexer for passing an analog charge information signal, which is charge information read out from each pixel of the radiation detector, alternately in a first order and a second order opposite to the first order; an analog signal amplifier for amplifying the analog charge information signal that has passed through the analog multiplexer; an analog/digital converter for converting the analog charge information signal to a corresponding digital charge information signal; a signal correcting unit for using one of a first digital charge information signal corresponding to the analog charge information signal that has passed through the analog multiplexer in the first order and a second digital charge information signal corresponding to the analog charge information signal that has passed through the analog multiplexer in the second order, to correct the other of the first digital charge information signal and the second digital charge information signal.

According to the invention, one of the first and second digital charge information signals is used to correct the other. Here, the first and second digital charge information signals correspond to analog charge information signals which have passed through the analog multiplexer in the first order and the second order that is opposite to the first order, respectively. As a result, it is possible to reduce both the effect of noise on the radiation image information when switching between signals in the analog multiplexer and the effect on the radiation image information, of poor responsiveness of the analog amplifier provided downstream of the analog multiplexer. Thus, it is possible to prevent the deterioration in image quality without increasing the number of analog/digital converter.

In the above-described arrangement, the first order may be one of an ascending order and a descending order along an arrangement direction of the plurality of pixels and the second order may be the other of the ascending order and the descending order.

Further, it is preferable that the analog multiplexer reads out, for each line of the pixels, the charge information along an arrangement direction of the pixels in both the first order and the second order, and that the signal correcting unit uses, for each line of the pixels, one of the first digital charge information signal outputted in the first order and the second digital charge information signal outputted in the second order, to correct the other of the first digital charge information signal and the second digital charge information signal.

With this arrangement, it is possible to make use of both the first and second digital charge information signals output from the analog multiplexer in the first order and the second orders for each line of pixels. Ideally, the first and second digital charge information signals would have identical waveforms. However, in reality, the noise when the analog multiplexer switches between signals, the poor responsiveness of the output amplifier and other such effects mean that the two digital charge information signals are not identical. It is therefore possible to make use of the two digital charge information signals to correct for the above-described harmful influences on the digital charge information signals.

The analog multiplexer may read out, for each line of the pixels, the charge information along an arrangement direction of the pixels, while alternating the first order and the second order from line to line, and the signal correcting unit may use, with respect to the pixels which are adjacent in the arrangement direction, one of the first digital charge information signal which has been output in the first order and the second digital charge information signal which has been output in the second order, to correct the other of the first digital charge information signal and the second digital charge information signal.

In radiation images, the brightness distribution is generally uneven and so the charge information is likely to be identical for pixels which are adjacent in the arrangement direction. When the charge information of pixels adjacent in the arrangement direction is identical, it is possible to correct for the various harmful influences on the digital charge information signals by outputting the digital charge information signal corresponding to one of the pixels in either the first or second order, outputting the digital charge information signal corresponding to the other of the pixel in the opposite order, and making use of the two digital charge information signals.

It is further preferable that, when a difference in the charge information between the pixels adjacent in the arrangement direction exceeds a threshold value, the signal correcting unit uses one of the first digital charge information signal and the second digital charge information signal, to correct the other of the first digital charge information signal and the second digital charge information signal. Note that when there is no difference between the charge information of the pixels which are adjacent in the arrangement direction, the charge information of the pixels may be considered to be identical. When the charge information is identical, the amplitude of the digital charge information signal is considered to be unchanged. Thus, there is no need to compare the digital charge information signal of the current line to digital charge information signal of another line to correct the digital charge information signal of the current line. Hence, when the charge information is identical in the adjacent pixels, the processing load and power consumption can be reduced by omitting the correction.

The signal correcting unit may correct a section of one of the first digital charge information signal and the second digital charge information signal by replacing the section with a section of the other of the first digital charge information signal and the second digital charge information signal.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
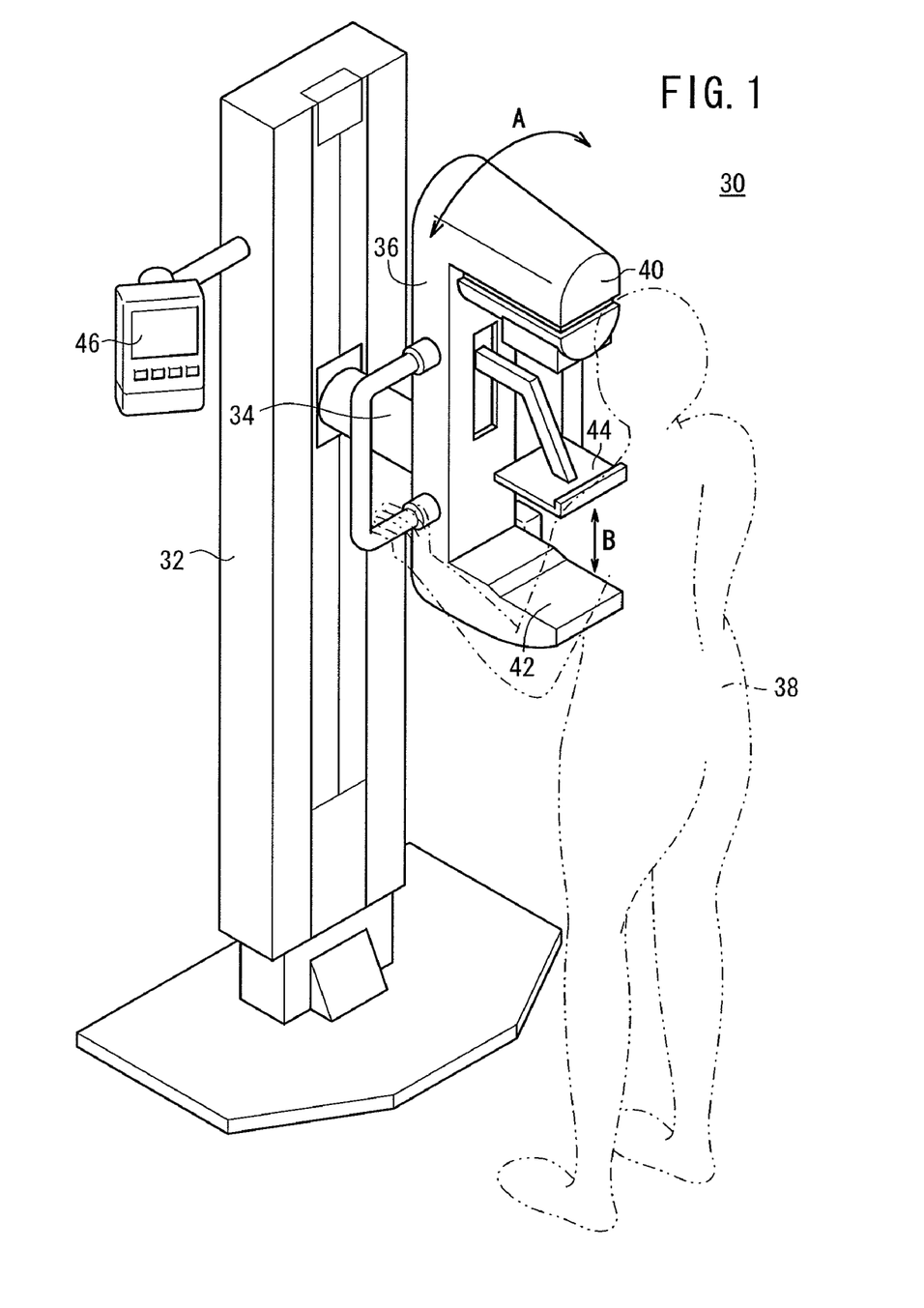
FIG. 1 is a perspective view of a mammography apparatus forming a radiation image capturing apparatus according to an embodiment of the present invention.

1. Configuration of Radiation Image Capturing Apparatus (mammography apparatus 30)
(1) Basic Configuration FIG. 1 is a perspective view of a radiation image capturing apparatus according to an embodiment of the present invention, which is a mammography apparatus 30 used in breast cancer screening and the like.

The mammography apparatus 30 includes an upstanding base 32, an arm 36 fixed to a pivot shaft 34 that is connected substantially centrally to the base 32, a radiation source housing unit 40 fixed to one end of the arm 36 and housing a radiation source (not shown) for applying radiation X, or electromagnetic waves for recording, to a breast 39 (see FIG. 2) which is the image capturing site of a subject 38, an image capturing base 42 fixed to the other end of the arm 36 so as to oppose the radiation source housing unit 40, and a compression plate 44 for holding the breast 39 by compressing it against the image capturing base 42.

The arm 36 holding the radiation source housing unit 40 and the image capturing base 42 can be rotated about the pivot shaft 34 in the directions indicated by double-headed arrow A to adjust the image capturing direction with respect to the breast 39 of the subject 38. The compression plate 44 is connected to the arm 36 between the radiation source housing unit 40 and the image capturing base 42 so as to be movable in the directions shown by double-headed arrow B.

The base 32 is also provided with a display control panel 46 for displaying image capturing information of the image obtained by the mammography apparatus 30 and the identification information (ID) or the like of the subject 38. The image capturing information includes the image capturing site, image capturing direction, and the like for the image of the subject 38 to be captured by the mammography apparatus 30. The display control panel 46 may, where necessary, further allow settings relating to the image capturing information and ID information.

(2) Image Capturing Base 42

Figure 2:
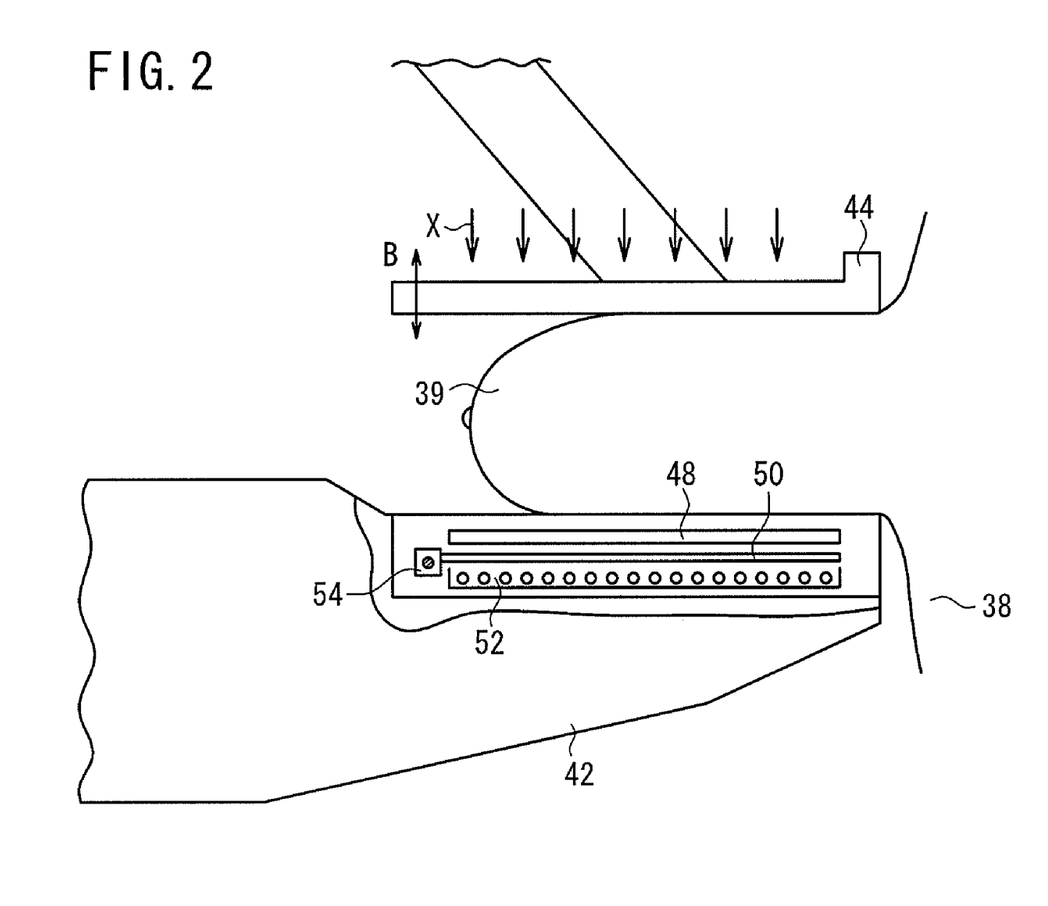
FIG. 2 is a view showing a main portion of an internal structure of an image capturing base in the mammography apparatus shown in FIG. 1.

FIG. 2 is a partially cross-sectional view of a main part of the mammography apparatus 30, showing the internal structure of the image capturing base 42. FIG. 2 shows the breast 39, i.e., the image capturing site of the subject 38, being placed between the image capturing base 42 and the compression plate 44.

Contained within the image capturing base 42 is a radiation detector 48. The radiation detector 48 stores radiation image information captured based on the radiation X emitted from the radiation source in the radiation source housing unit 40 and generates electric signals corresponding to the radiation image information. Also contained within the image capturing base 42 is a linear reading light source 50 that applies linear reading light L (reading electromagnetic waves, see FIG. 3) to the radiation detector 48 in order to read out the recorded radiation image information from the radiation detector 48. Further disposed within the image capturing base 42 is an erasing light source 52 that applies erasing light to the radiation detector 48. The reading light source 50 is scanned over the radiation detector 48 in a direction perpendicular to the plane of FIG. 2 (the direction indicated by the arrow C in FIG. 3) by a scanning mechanism 54. Note that, hereinafter, the direction indicated by the arrow C in FIG. 3 is also called the "sub(auxiliary)-scanning direction" and the longitudinal direction of the reading light source 50 (indicated by the arrow D in FIG. 3) is also called the "main scanning direction".

(3) Radiation Detector 48

The radiation detector 48 is a direct-conversion, light readout type solid-state detector. The radiation detector 48 stores radiation image information generated based on the radiation X that has passed through the breast 39 as an electrostatic latent image. Further, when scanned by the reading light L from the reading light source 50, the radiation detector 48 generates an electric current corresponding to the electric charges of the electrostatic latent image as charge information.

Figure 3:
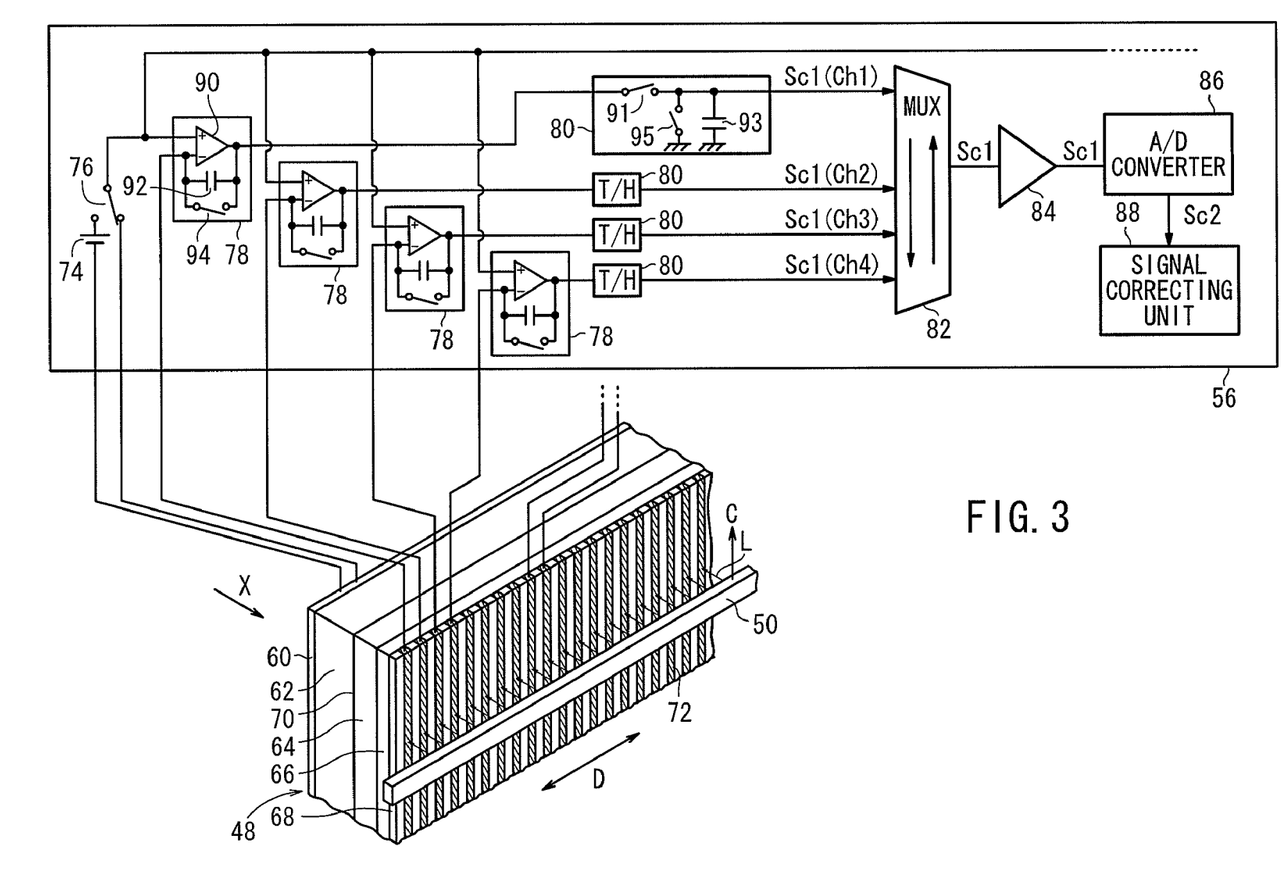
FIG. 3 is a diagram illustrating a detection processing circuit included in the radiation detector provided within the image capturing base shown in FIG. 2.

FIG. 3 is a diagram illustrating a detection processing circuit of the radiation image information, which is made up of the radiation detector 48, the reading light source 50 which applies the reading light L to the radiation detector 48, and a radiation image information processor 56 (hereinafter referred to as a "processor 56") for processing the radiation image information outputted from the radiation detector 48.

The radiation detector 48 can, for instance, be configured in the same way as the radiation detector shown in FIG. 7 of Japanese Laid-Open Patent Publication No. 2000-287034. The radiation detector 48 includes, in the stated order from the side directly exposed to the radiation X, a first electrode layer 60 which is transparent to the radiation X that has passed through the breast 39 of the subject 38, a recording photoconductive layer 62 which is rendered conductive by irradiation with the radiation X, a charge transport layer 64 which substantially acts as an insulator to the latent image charges and substantially acts as a conductor to transfer charges which are of opposite polarity to the latent image charges, a reading photoconductive layer 66 which is rendered conductive by irradiation with the reading light L from the reading light source 50, and a second electrode layer 68 which is transparent to the reading light L.

A charge portion 70 which stores the charges generated by the recording photoconductive layer 62 is formed at the interface between the recording photoconductive layer 62 and the charge transport layer 64. The second electrode layer 68 includes multiple linear electrodes 72 which extend in the direction of the arrow C (sub-scanning direction), perpendicular to the reading light source 50 which extends in the direction of the arrow D (main scanning direction). The linear electrodes 72 are connected to the processor 56 which reads out the charge information associated with the latent image charges stored in the charge portion 70 and processes the readout charge information.

As shown in FIG. 3, the processor 56 includes a power source 74, a switch 76, a plurality of current detecting amplifiers 78, a plurality of track and hold circuits (T/H circuits) 80, an analog multiplexer (analog MUX) 82, an output amplifier 84, an analog/digital converter (A/D converter) 86, and a signal correcting unit 88.

The power source 74 applies a predetermined voltage between the first electrode layer 60 and the second electrode layer 68 of the radiation detector 48. The switch 76 switches a connection to the power source 74 between the first electrode layer 60 and the second electrode layer 68.

The current detecting amplifiers 78 are connected to corresponding linear electrodes 72 and detect the radiation image information represented by the latent image charges as electrical currents. Each current detecting amplifier 78 includes an operational amplifier 90, an integrating capacitor 92 and a switch 94. The linear electrode 72 is connected to the inverting input terminal of the operational amplifier 90, and the power source 74 is connected to the non-inverting input terminal of the operational amplifier 90 via the switch 76.

Each T/H circuit 80 stores the radiation image information that has been detected by the current detecting amplifier 78. Thus, on reception of a signal for the beginning of sampling from a timing control circuit (not shown), a switch 91 in each T/H circuit is switched ON and voltage from the integrating capacitor 92 of the current detecting amplifier 78 accumulates on a capacitor 93 (track mode). On receiving a hold signal from the timing control circuit, the switch 91 in each T/H circuit 80 is switched OFF and voltage across the capacitor 93 is held (hold mode). To reset the voltage value of the capacitor 93, a switch 95 is switched ON.

The analog MUX 82 selects the T/H circuits 80 in an order described in a later section based on a selection signal from the timing control circuit, and passes to the output amplifier 84 an analog charge information signal Sc1 containing the radiation image information (charge information) which has been output from the selected T/H circuits 80.

The output amplifier 84 amplifies the analog charge information signal Sc1 output from the T/H circuits 80 using a predetermined gain. Next, the A/D converter 86 converts the amplified analog charge information signal Sc1 and outputs a digital charge information signal Sc2. Here, the A/D conversion is performed by converting the charge information, each piece of which represents a brightness level, to a gray-scale of 256 gradations. The signal correcting unit 88 corrects the digital charge information signal Sc2 using a method which is described in a later section. After correction by the signal correcting unit 88, the digital information signal Sc2 is transmitted to a signal processing apparatus (not shown), and used in processing for display of the radiation image.

(4) Reading Light Source 50

Figure 4:
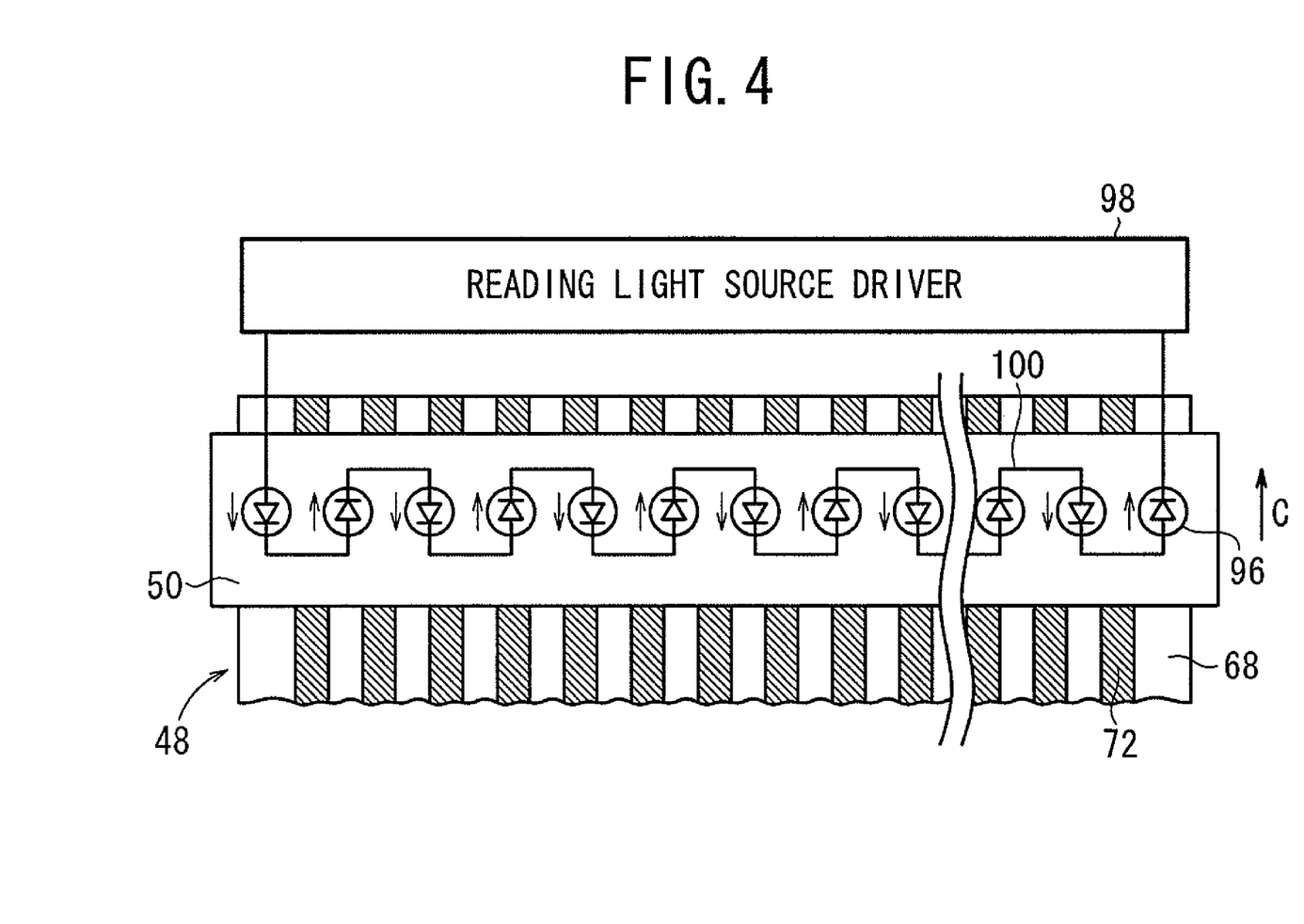
FIG. 4 is a diagram illustrating the wiring circuit of a reading light source which applies reading light to the radiation detector shown in FIG. 3.

FIG. 4 is schematic view of the reading light source 50. The reading light source 50 includes a plurality of light emitting devices 96 disposed in the main scanning direction and a reading light source driver 98 which supplies a driving current to the light emitting devices 96. Note that the main scanning direction is the direction in which the linear electrodes 72 forming the second electrode layer 68 of the radiation detector 48 are disposed and is perpendicular to a movement direction of the reading light source 50 (sub-scanning direction) indicated by the arrow C. In the example shown in FIG. 4, the light emitting devices 96 are connected in series by a wiring circuit 100 and are configured so that the current in all the light emitting devices 96 flows parallel the longitudinal directions of the linear electrodes 72 and currents in adjacent light emitting devices 96 flow in opposite directions. Note that LEDs or the like can be used as the light emitting devices 96.

2. Method for Generating Radiation Image

The operation of the mammography apparatus 30 of the present embodiment with the above configuration will now be described.

(1) Preparations for Image Capture

First, ID information about the subject 38, image capturing conditions and the like are provided to the mammography apparatus 30 by means of a console (not shown), an ID card, or the like. The ID information may include the name, age, gender, etc. of the subject 38 and can be acquired from an ID card of the subject 38. If the mammography apparatus 30 is connected to a network, the ID information may also be acquired from other apparatuses on the network. The image capturing conditions may include an image capturing site, an image capturing direction, and the like specified by the physician. These items of information may be acquired from a higher-level apparatus on the network or be entered through the console by a radiologist. The ID information, image capturing conditions, and the like may be displayed on the display control panel 46 of the mammography apparatus 30 for verification.

The radiologist then sets the mammography apparatus 30 in accordance with the specified image capturing conditions. The image capturing directions of the breast 39 may include, for example, a craniocaudal view (CC), a mediolateral view (ML), and a mediolateral oblique view (MLO), for which image capture is performed by exposing the breast 39 to the radiation X from the top, side, and an oblique angle respectively. The arm 36 is rotated about the pivot shaft 34 in accordance with the specified image capturing direction.

Next, the breast 39 of the subject 38 is positioned with respect to the mammography apparatus 30, i.e., the breast 39 is placed on the image capturing base 42 and the compression plate 44 is moved down to hold the breast 39 between the image capturing base 42 and the compression plate 44 (see FIG. 2).

(2) Recording to the Radiation Detector

After the above preparatory operations have been completed, the radiation source (not shown) in the radiation source housing unit 40 is activated to expose the breast 39 to the radiation X in accordance with the set image capturing conditions. At this point, the radiation detector 48 housed in the image capturing base 42 applies a predetermined voltage between the first electrode layer 60 and the second electrode layer 68 by connecting the switch 76 shown in FIG. 3 to the power source 74.

The radiation X that has passed through the breast 39 irradiates the recording photoconductive layer 62 through the first electrode layer 60 of the radiation detector 48. Under irradiation, the recording photoconductive layer 62 generates charge pairs and exhibits conductivity. The positive charge of the charge pair couples with the negative charge provided to the first electrode layer 60 from the power source 74 and disappears. Meanwhile, the negative charges generated in the recording photoconductive layer 62 move toward the charge transport layer 64. Since the charge transport layer 64 substantially acts as an insulator to the negative charge, the negative charges are accumulated in the charge portion 70 formed at the interface between the recording photoconductive layer 62 and the charge transport layer 64 to define a latent image.

(3) Reading Out from Radiation Detector

After the latent image has been recorded to the radiation detector 48, the processor 56 reads out the radiation image information. First, the switch 76 of the processor 56 is operated to connect the non-inverting input of the operational amplifier 90 in the current detecting amplifier 78 to the first electrode layer 60 of the radiation detector 48.

The readout of the radiation image information, which is the charge information representing the latent image, is carried out by driving the scanning mechanism 54 (FIG. 2) to move the reading light source 50 in the direction of arrow C (the sub-scanning direction) and thereby scanning the reading light L over the reading photoconductive layer 66, while switching the switch 94 of the current detecting amplifier 78 ON and OFF in accordance with a predetermined pixel pitch in the sub-scanning direction. It should be noted that the charge information from a given linear electrode 72 read out in a given ON-OFF cycle is the charge information from a single pixel and the collection of charge information from all the linear electrodes in a given ON-OFF cycle is the charge information for a single line.

To read out the radiation image information, a driving current is supplied from the reading light source driver 98 to the light emitting devices 96 of the reading light source 50. Applying the reading light L output from the light emitting devices 96 to the reading photoconductive layer 66 through the second electrode layer 68 causes the reading photoconductive layer 66 to generate charge pairs and exhibit conductivity. The positive charges of the charge pairs move through the charge transport layer 64, which substantially acts as a conductor to positive charge, and arrive at the charge portion 70. In the charge portion 70, the positive charges couple with the negative charges that make up the latent image stored in the charge portion, and disappear. Meanwhile, the negative charges in the reading photoconductive layer 66 couple with the positive charges in the linear electrode 72 of the second electrode layer 68, and disappear. A current is generated in the linear electrode 72 as the charges disappear, and the current is read out by the processor 56 as the charge information representing the radiation image information.

The current generated in each linear electrode 72 is integrated by the operational amplifier 90 of the corresponding current detecting amplifier 78 and supplied to the T/H circuit 80 as a voltage signal. In track mode, the T/H circuit 80 accumulates the voltage representing the charge information across the capacitor 93 after the switch 91 has been switched ON. Then, when the switch 91 is switched OFF, the T/H circuit 80 switches into the hold mode and the voltage, which represents the charge information, is temporarily held on the capacitor 93.

When the T/H circuits 80 are in the hold mode, the voltage value held on the T/H circuit 80 selected by the analog MUX 82 is output via the analog MUX 82 as the analog charge information signal Sc1. The present embodiment has two modes, i.e., first and second modes corresponding to different orders in which the analog MUX 82 selects the signal path (i.e., the order in which the analog charge information signals Sc1 (Ch1, Ch2 . . . ) are accepted from the T/H circuits 80). In the first mode (hereinafter referred to as the "first readout mode"), the readout is performed in both ascending order and descending order for each line. In the second mode (hereinafter referred to as the "second readout mode"), the readout alternates between ascending and descending order from line to line.

Here, "one line" means the group of portions (pixels), on the linear electrodes 72, which have been irradiated with the reading light L from the reading light source 50. A single piece of charge information is output from each pixel. When charge information is read out from each pixel of the line, the reading light source 50 is moved one line in the direction of the arrow C (sub-scanning direction), and charge information is read out from each pixel in the next line.

Figure 5:
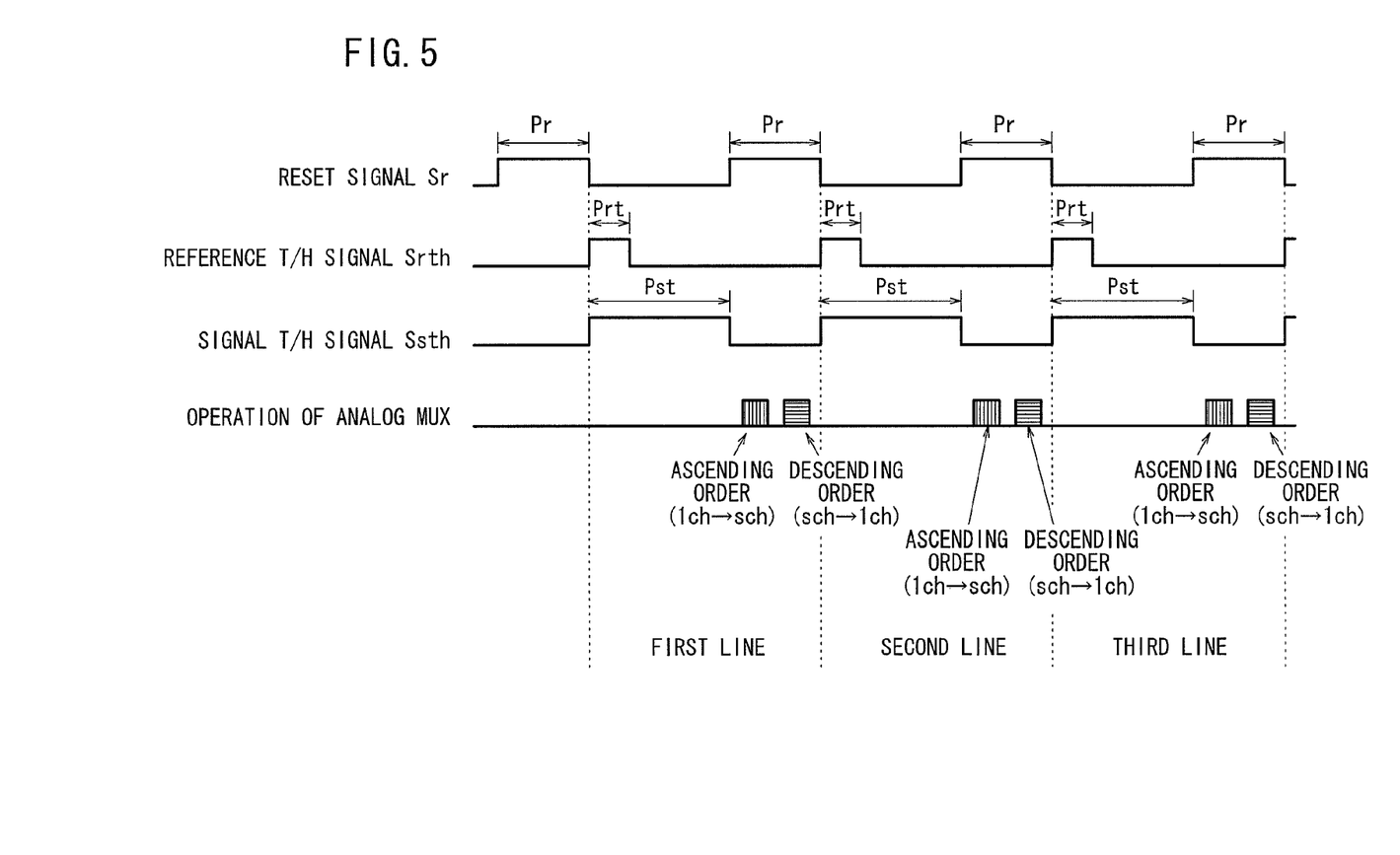
FIG. 5 is a timing chart for various signals of a first reading mode used in the detection processing circuit and operations of an analog multiplexer shown in FIG. 3.

FIG. 5 is a timing chart for the first readout mode. When a reset signal Sr for switching ON the switch 94 is output to the current detecting amplifiers 78 for a predetermined period (reset period Pr), the switch 94 of the current detecting amplifier 78 is switched ON and the voltage value of the integrating capacitor 92 is reset.

Next, triggered by the end of the reset period Pr (i.e., on the falling edge of the reset signal Sr), the first line is irradiated with the reading light L from the reading light source 50, and a reference track/hold signal (reference T/H signal) Srth and signal track/hold signal (signal T/H signal) Ssth are output to each T/H circuit 80. The reference T/H signal Srth defines the period over which the capacitor 93 of each T/H circuit 80 is reset, and is the period over which the switch 95 is ON (reference track period Prt). The signal T/H signal Ssth defines the period over which each T/H circuit 80 detects the signal level from the current detecting amplifier 78 and is the period over which the switch 91 is ON (signal track period Pst). The signal track period Pst defines the period of the sample mode. Using the reference T/H signal Srth in combination with the signal T/H signal Ssth allows a noise level to be subtracted from the voltage level stored on the capacitor 93 of the T/H circuit 80, and allows the signal level from the current detecting amplifier 78 to be detected. These signals are processed using Correlated Double Sampling (CDS). After irradiating the first line with the reading light L, the reading light source 50 moves to a position corresponding to the second line before the next reset signal Sr is transmitted.

After the signal track period Pst, the charge information from the T/H circuit 80 selected by the analog MUX 82 is read out. In the present embodiment, when reading out the charge information from the T/H circuits 80 storing the charge information of the first line, the analog MUX 82 reads out the charge information starting with the T/H circuit 80 corresponding to a first signal path (channel) and ending with the T/H circuit 80 corresponding to the $s^{th}$ channel (i.e., in the ascending order (1, 2, 3, . . . s−2, s−1, s)), where "s" is the number of channels used by the processor 56. Next, for the same first line, the analog MUX 82 reads out the charge information starting with the T/H circuit 80 corresponding to the $s^{th}$ channel and ending with the T/H circuit 80 corresponding to the first channel (i.e., in the descending order (s, s−1, s−2, . . . 3, 2, 1)). Thereafter, each line of the charge information is read out in both ascending and descending orders.

Figure 6:
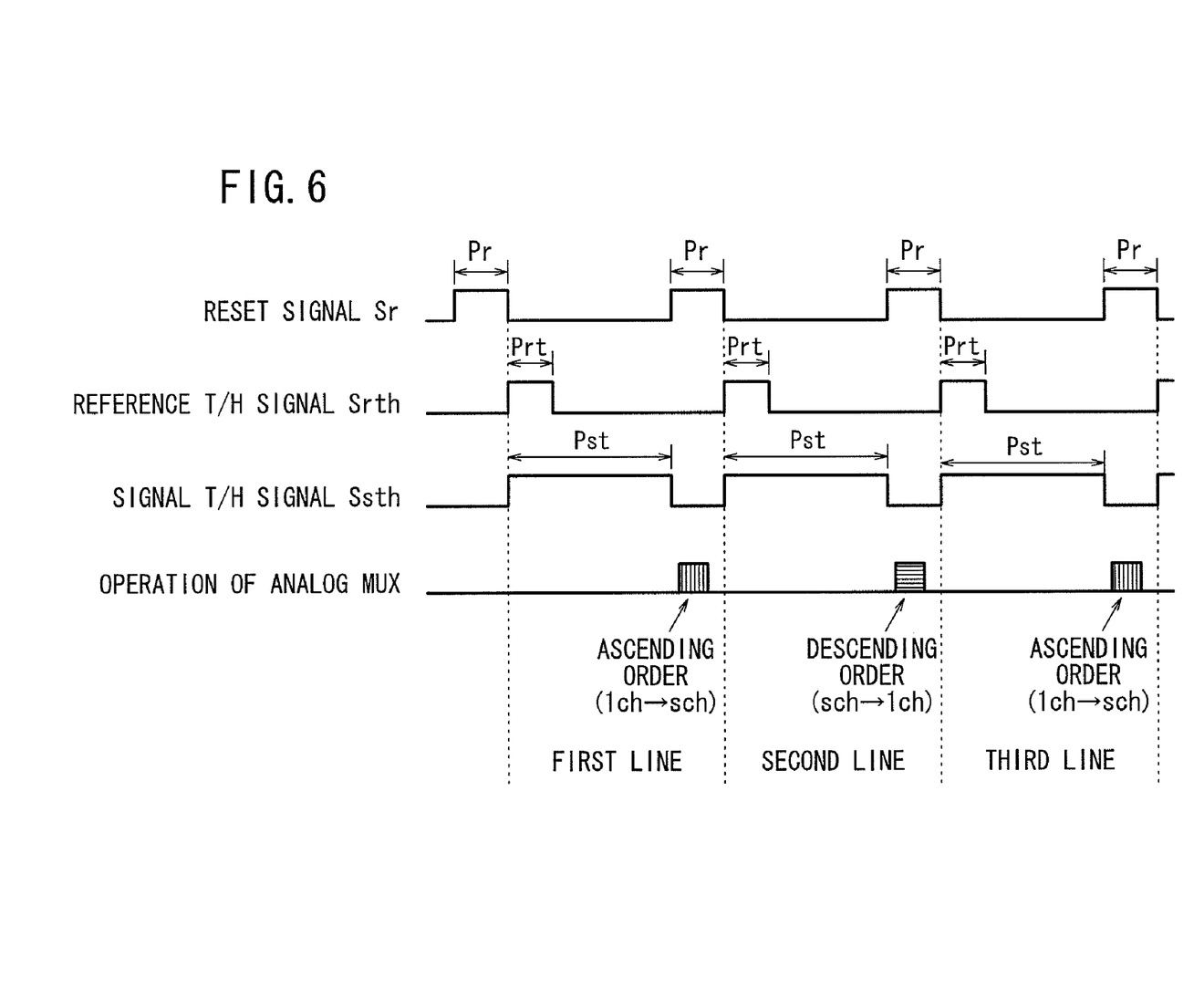
FIG. 6 is a timing chart for various signals of a second reading mode used in the detection processing circuit and operations of the analog multiplexer shown in FIG. 3.

FIG. 6 is a timing chart for the second readout mode. In the second readout mode, the processing is performed in substantially same way as in the first readout mode. However, whereas in the first readout mode the charge information is read out in both ascending and descending orders for each line, in the second readout mode the charge information of each line is read out in either ascending order or descending order.

The analog charge information signal Sc1 from the analog MUX 82 is supplied to the output amplifier 84. The output amplifier 84 amplifies the analog charge information signal Sc1 using a predetermined gain. The analog charge information signal Sc1 amplified by the output amplifier 84 is converted to the digital charge information signal Sc2 by the A/D converter 86.

The digital charge information signal Sc2 output from the A/D converter 86 undergoes the correction processing described below in the signal correcting unit 88.

Figure 7A:
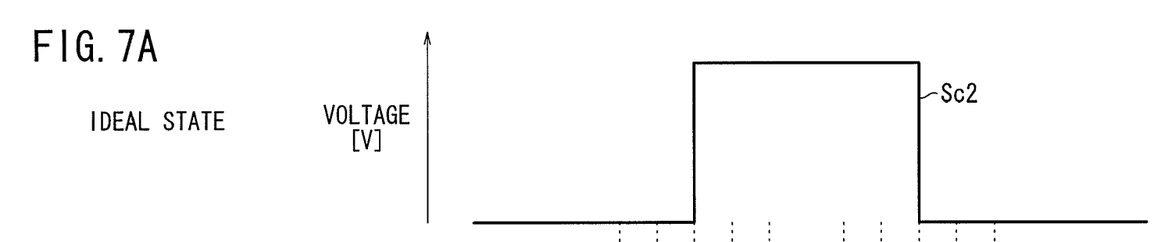
FIGS. 7A, 7B, 7C are diagrams illustrating correction processing used in the detection processing circuit shown in FIG. 3.
Figure 7B:
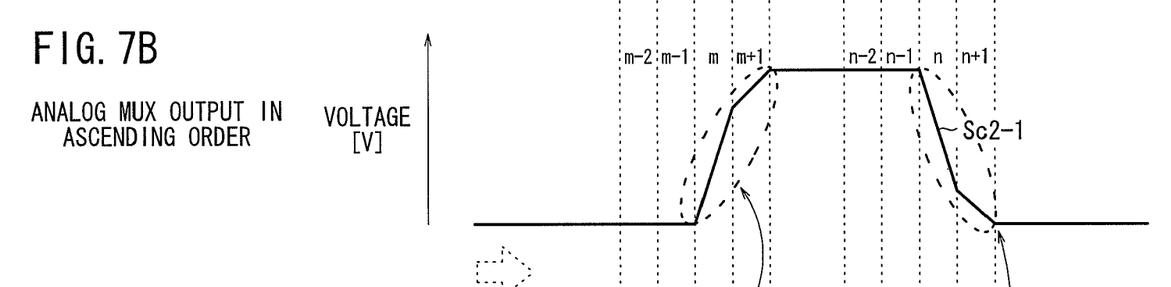
Figure 7C:
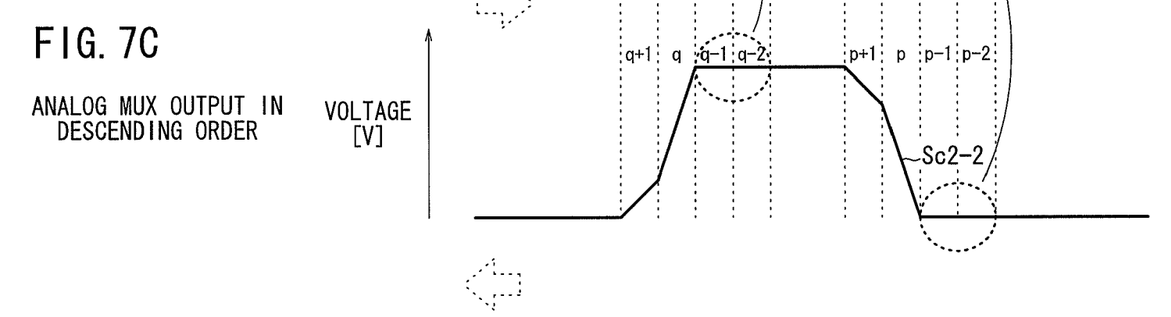

FIG. 7A shows, for a given line, the waveform of the digital charge information signal Sc2 that would be produced by an ideal digitization of the analog charge information signals Sc1 that have been output from the T/H circuits 80 but not yet input to the analog MUX 82. FIG. 7B shows, for the same line, the waveform of the digital charge information signal Sc2 to be input to the signal correcting unit 88. Here, the digital charge information signal Sc2 is the result of A/D conversion of the analog charge information signal Sc1 from the analog MUX 82 when the channels are read out in the ascending order (hereinafter referred to as "first digital charge information signal Sc2-1"). FIG. 7C shows, for the same line, the waveform of the digital charge information signal Sc2 to be input to the signal correcting unit 88. Here, the digital charge information signal Sc2 is the result of A/D conversion of the analog charge information signal Sc1 from the analog MUX 82 when the channels are read out in the descending order (hereinafter referred to as "second digital charge information signal Sc2-2"). Thus, FIG. 7B and FIG. 7C show the waveforms outputted as the digital charge information signal Sc2 in the above-described first readout mode.

In comparison to ideal waveform of FIG. 7A, the ascending order waveform (first digital charge information signal Sc2-1) of FIG. 7B takes longer to reach the peak value and return to the bottom value due to factors such as the slow response of the output amplifier 84. Thus, while the waveform of FIG. 7A reaches the peak value immediately upon entering the $m^{th}$ region, the ascending order waveform does not reach the peak value until the end of the $m+1^{th}$ region. Further, while the waveform of FIG. 7A returns from the peak value to the bottom value immediately upon entering the $n^{th}$ region, the ascending order waveform does not return to the bottom value until the end of the $n+1^{th}$ region due to factors such as the slow response of the output amplifier 84.

Similarly, in comparison to the ideal waveform of FIG. 7A, the descending order waveform (second digital charge information signal Sc2-2) of FIG. 7C takes longer to reach the peak value and return to the bottom value due to factors such as the responsiveness of the output amplifier 84. Thus, while the ideal waveform reaches the peak value immediately upon entering the $p^{th}$ region, the descending order waveform does not reach the peak value unit the end of the $p+1^{th}$ region. Further, while the ideal waveform returns from the peak value to the bottom value immediately upon entering the $q^{th}$ region, the descending order waveform does not return to the bottom value until the end of the $q+1^{th}$ region due to factors such as the responsiveness of the output amplifier 84.

It should be noted that the forward direction of time is plotted left to right in FIG. 7B and plotted right to left in FIG. 7C. Also, the forward direction of time in FIG. 7A is from left to right when comparing FIG. 7A and FIG. 7B, and from right to left when comparing FIG. 7A and FIG. 7C. Note also that, when the processor 56 is in the first readout mode, regions having identical positions on the horizontal axes in FIG. 7B and FIG. 7C show the charge information for the same pixel. For instance, the $m+1^{th}$ region and the $q-2^{th}$ region both contain charge information for the same pixel. Moreover, when the processor 56 is in the second readout mode, regions having identical positions on the horizontal axes in FIG. 7B and FIG. 7C show the charge information for adjacent pixels in the sub-scanning direction (direction of arrow C). For instance, the $m+1^{th}$ region and the $q-2^{th}$ region show charge information for two pixels from lines which are adjacent in the sub-scanning direction.

According to the present embodiment, the sections of the ascending order waveform of FIG. 7B (first digital charge information signal Sc2-1) where the response is slow (i.e., in the $m^{th}$ and $m+1^{th}$ regions and the $n^{th}$ and $n+1^{th}$ regions) are replaced with the corresponding sections of the descending order waveform of FIG. 7C (the second digital charge information signal Sc2-2). In other words, the waveform sections in the $m^{th}$ and $m+1^{th}$ regions and the $n^{th}$ and $n+1^{th}$ regions are replaced with the waveform sections of the $q-2^{th}$ and $q-1^{th}$ regions and the $p-2^{th}$ and $p-1^{th}$ regions, respectively. The waveform obtained with this technique closely resembles the ideal waveform shown in FIG. 7A.

In the above-described correction processing, sections of the first digital charge information signal Sc2-1 were replaced with sections of the second digital charge information signal Sc2-2. However, other correction processing may be used. For example, the first and second digital charge information signals Sc2-1 and Sc2-2 may be averaged, or weights may be applied according to the acquisition timing of the signal.

It is also to be noted that the above-described correction processing is effective when applied to adjacent pixels which are in the same line and hold differing charge information. When the adjacent pixels hold the same charge information, the signal amplitude is identical for both pixels and so the slow response of the type described above does not occur. Hence, the signal correcting unit 88 may calculate the difference between the charge information held by adjacent pixels and only apply the above-described correction processing when the difference exceeds a threshold value. Moreover, the threshold value may vary. For example, the threshold value may vary according to the gain (amplitude) used for the ascending order waveform of FIG. 7B.

When the radiation image information for a complete line in the sub-scanning direction has been read out, the switch 94 of the current detecting amplifier 78 is switched ON and the charged stored in the integrating capacitor 92 is discharged. The charge stored in the capacitor 93 is also discharged by switching ON the switch 95 with the switch 91 of the T/H circuit 80 in an OFF state. The above operations are repeated while moving the reading light source 50 in the direction of the arrow C (sub-scanning direction) to achieve two-dimensional readout of the radiation image information recorded as stored charge by the radiation detector 48.

3. Advantages of the Present Embodiment

As described above, in the present embodiment, the analog MUX 82 alternates between the ascending and descending channel orders when passing the plurality of analog charge information signals Sc1 (Ch1 to Chs). The analog charge information signal Sc1 output from the analog MUX 82 is then amplified by the output amplifier 84 and converted to the digital charge information signal Sc2 by the A/D converter 86. The signal correcting unit 88 then compares the first digital charge information signal Sc2-1, which corresponds to the analog charge information signal Sc1 output from the analog MUX 82 when the channels are read out in ascending order, with the second digital charge information signal Sc2-2, which corresponds to analog charge information signal Sc1 output from the analog MUX 82 when the channels are read out in descending order, and corrects the first digital charge information signal Sc2-1 based on the result of the comparison.

Thus, according to the present embodiment, the first digital charge information signal Sc2-1 is corrected based on the result of the comparison between the first and second digital charge information signals Sc2-1 and Sc2-2 which correspond to the analog charge information signal Sc1 output from the analog MUX 82 when the channels are read out in ascending and descending orders, respectively. Hence, it is possible to reduce the effects on the radiation image information of noise when the analog MUX 82 is switching between signals and the effects on the radiation image information of the slow response of the output amplifier 84 provided downstream of the analog MUX 82. Thus, it is possible to prevent the deterioration in image quality. In particular, at edge portions in the radiation image where there is a large difference in amplitude (change in brightness), it is possible to correct for the poor responsiveness of the output amplifier 84 and thereby suppress blurring and lack of sharpness of the radiation image.

Moreover, since the output amplifier 84 and the A/D converter 86 are provided downstream of the analog MUX 82, the analog charge information signal Sc1 output from the analog MUX 82 can be processed in the conventional order. As a consequence, the number of required output amplifiers 84 and A/D converters 86 can be reduced, and a reduction in space and cost can be achieved.

In the first readout mode, the analog MUX 82 reads out the electric charge information from the T/H circuits 80 in each line in both ascending and descending order, and the signal correcting unit 88 compares the first and second digital charge information signals Sc2-1 and Sc2-2 which have been read out from the channels in ascending and descending orders, respectively, and corrects the first digital charge information signal Sc2-1 based on the results of the comparison.

With this arrangement, the results of the comparison of the first and second digital charge information signals Sc2-1 and Sc2-2 which have been read out from the channels in ascending and descending orders, respectively, can be applied to each line. Ideally, the first and second digital charge information signals Sc2-1 and Sc2-2 would be identical, but in reality the noise when the analog MUX 82 switches between signals, the poor responsiveness of the output amplifier 84 and other such effects mean that the first and second digital charge information signals Sc2-1 and Sc2-2 are not identical. By using the results of the comparison of the first and second digital charge information signals Sc2-1 and Sc2-2, it is therefore possible to correct for various harmful influences on the first and second digital charge information signals Sc2-1 and Sc2-2.

In the second readout mode, the analog MUX 82 alternates between reading out in the ascending order and the descending order so that adjacent lines are read out in opposing order. The signal correcting unit 88 then compares the first and second digital charge information signals Sc2-1 and Sc2-2 from the channels in ascending and descending orders respectively, for pixels which are adjacent in an arrangement direction (direction of the arrow D), and corrects the first digital charge information signal Sc2-1 based on the results of the comparison.

In radiation images, the brightness distribution is generally uneven and so it is likely that the charge information will be identical for pixels which are adjacent in the arrangement direction. When the charge information of two given pixels which are adjacent in the pixel arrangement direction is identical, the first digital charge information signal Sc2-1 corresponding to one pixel is output in the ascending order, the second digital charge information signal Sc2-2 corresponding to the other pixel is output in the descending order, and the first and second digital charge information signals Sc2-1 and Sc2-2 can be compared to enable correction of the various harmful influences on the first and second digital charge information signals Sc2-1 and Sc2-2.

When, on the other hand, the difference between the charge information of the two given pixels which are adjacent in the pixel arrangement direction is larger than a predetermined threshold value, the signal correcting unit 88 corrects the first digital charge information signal Sc2-1. Note that, for example, when there is no difference between the charge information of two pixels which are adjacent in the arrangement direction, the charge information at the two pixels may be considered to be identical. If the charge information is identical at two pixels, the amplitude is unchanged at corresponding positions in the first and second digital charge information signals Sc2-1 and Sc2-2. In this case, there is no need to correct the digital charge information signal of a current line (i.e., the first digital charge information signal Sc2-1) through comparison with the digital charge information signal Sc2 of another line (i.e., the second digital charge information signal Sc2-2). Hence, when the charge information is identical in the two adjacent pixels, the processing load and power consumption can be reduced by omitting the correction.

4. Modifications

The invention is not limited to the embodiment described above. Various changes and modifications may be made in light of the description herein without departing from the scope of the appended claims. For example the, invention can make use of any of the configurations (1) to (4) described below.

(1) Radiation Image Capturing Apparatus

The radiation image capturing apparatus is not limited to the mammography apparatus 30 of the above-described embodiment, and may be another type of radiation image capturing apparatus.

(2) Radiation Detector

Instead of the direct-conversion, light readout type radiation detector 48 used in the embodiment described above, a radiation detector of the indirect conversion type may be employed that includes a scintillator for temporarily converting radiation X into visible light, and a photoconductive recording layer that generates electrical charge pairs when exposed to the visible light. Alternatively, a radiation detector of the electric readout type may be utilized. For a radiation detector of the electric readout type, a TFT device, a CCD (Charge Coupled Device), a CMOS (Complementary Metal Oxide Semiconductor) device or the like may be used, where an analog multiplexer or the like is provided outside an image capturing portion.

(3) Analog MUX

In the above-described embodiment, the readout order of the charge information from the channels by the analog MUX 82 is alternated between the ascending order and the descending order of the channels. However, the readout order is not limited to this, and any readout order which alternates between a predetermined order (first order) and the direct opposite of the first order (second order) is acceptable.

Figure 8:
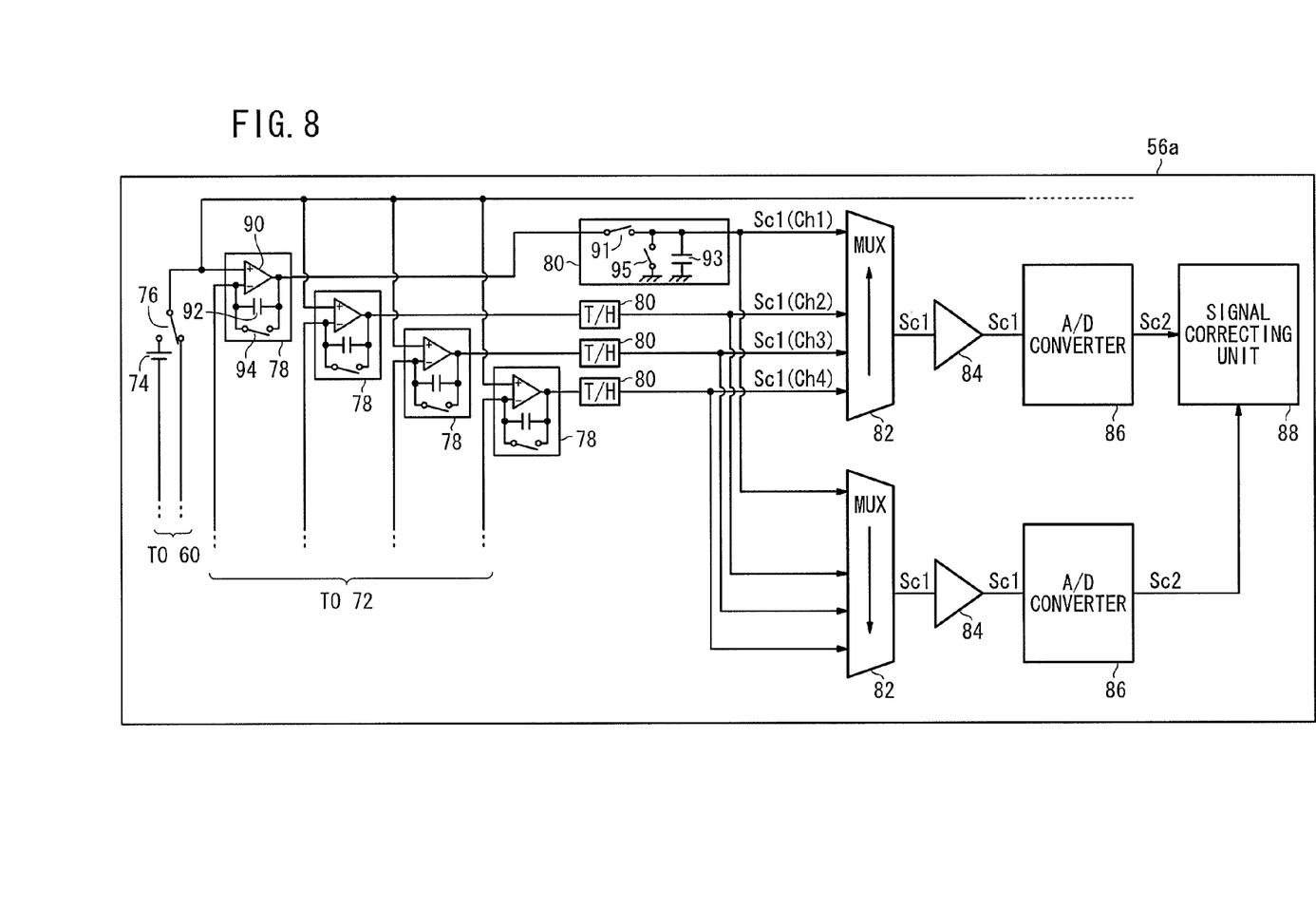
FIG. 8 is a schematic showing a modification of the detection processing circuit shown in FIG. 3.

In the present embodiment, a single analog MUX 82 was provided, but there is no limit on the number of analog MUX. For instance, the configuration shown in FIG. 8 in which a radiation image information processor 56a includes two analog MUXs 82 can be used. One of the analog MUX 82 reads out the charge information in the ascending order and the other reads out the charge information in the descending order. The two analog MUXs 82 transmit the charge information to the signal correcting unit 88 via the corresponding output amplifiers 84 and A/D converters 86.

(4) Reading Light Source, Reading Light

In the above-described embodiment, the reading light source 50 and the reading light L emitted from the reading light source 50 are both described as being linear. However, the reading light source 50 may be configured to emit a spot of light, and the spot of light may be used as the reading light L and scanned over the radiation detector.

What is claimed is:

1. A radiation image capturing apparatus, comprising:
   a radiation detector for detecting charge information representing radiation image information;
   an analog multiplexer for passing an analog charge information signal, which is charge information read out from each pixel of the radiation detector, alternately in a first order and a second order opposite to the first order;
   an analog signal amplifier for amplifying the analog charge information signal that has passed through the analog multiplexer;
   an analog/digital converter for converting the analog charge information signal to a corresponding digital charge information signal; and
   a signal correcting unit for using one of a first digital charge information signal corresponding to the analog charge information signal that has passed through the analog multiplexer in the first order and a second digital charge information signal corresponding to the analog charge information signal that has passed through the analog multiplexer in the second order, to correct the other of the first digital charge information signal and the second digital charge information signal.

2. The radiation image capturing apparatus according to claim 1, wherein the first order is one of an ascending order and a descending order along an arrangement direction of the pixels and the second order is the other of the ascending order and the descending order.

3. The radiation image capturing apparatus according to claim 1, wherein the analog multiplexer reads out, for each line of the pixels, the charge information along an arrangement direction of the pixels in both the first order and the second order, and
   the signal correcting unit uses, for each line of the pixels, one of the first digital charge information signal outputted in the first order and the second digital charge information signal outputted in the second order, to correct the other of the first digital charge information signal and the second digital charge information signal.

4. The radiation image capturing apparatus according to claim 3, wherein when a difference in the charge information between the pixels adjacent in the arrangement direction exceeds a threshold value, the signal correcting unit uses one of the first digital charge information signal and the second digital charge information signal, to correct the other of the first digital charge information signal and the second digital charge information signal.

5. The radiation image capturing apparatus according to claim 1, wherein the analog multiplexer reads out, for each line of the pixels, the charge information along an arrangement direction of the pixels, while alternating the first order and the second order from line to line, and
   the signal correcting unit uses, with respect to the pixels which are adjacent in the arrangement direction, one of the first digital charge information signal which has been output in the first order and the second digital charge information signal which has been output in the second order, to correct the other of the first digital charge information signal and the second digital charge information signal.

6. The radiation image capturing apparatus according to claim 5, wherein when a difference in the charge information between the pixels adjacent in the arrangement direction exceeds a threshold value, the signal correcting unit uses one of the first digital charge information signal and the second digital charge information signal, to correct the other of the first digital charge information signal and the second digital charge information signal.

7. The radiation image capturing apparatus according to claim 1, wherein the signal correcting unit corrects a section of one of the first digital charge information signal and the second digital charge information signal by replacing the section with a section of the other of the first digital charge information signal and the second digital charge information signal.

* * * * *